(12) United States Patent  
Rueter et al.

(10) Patent No.: US 7,831,303 B2  
(45) Date of Patent: Nov. 9, 2010

(54) CARDIAC PACING APPARATUS AND METHOD FOR CONTINUOUS CAPTURE MANAGEMENT

(75) Inventors: John C. Rueter, Woodbury, MN (US); William J. Combs, Minnetonka, MN (US)

(73) Assignee: Medtronic, Inc., Minneapolis, MN (US)

( * ) Notice: Subject to any disclaimer, the term of this patent is extended or adjusted under 35 U.S.C. 154(b) by 876 days.

(21) Appl. No.: 10/462,993

(22) Filed: Jun. 17, 2003

(65) Prior Publication Data

US 2004/0260352 A1    Dec. 23, 2004

(51) Int. Cl.
*A61N 1/365* (2006.01)

(52) U.S. Cl. .......................................... 607/27; 607/28
(58) Field of Classification Search .............. 607/27–28, 607/23
See application file for complete search history.

(56) References Cited

U.S. PATENT DOCUMENTS

| | | | |
|---|---|---|---|
| 4,257,423 A | 3/1981 | McDonald et al. | |
| 4,374,382 A | 2/1983 | Markowitz | |
| 4,428,378 A | 1/1984 | Anderson et al. | |
| 4,502,492 A | 3/1985 | Bornzin | |
| 5,003,975 A | 4/1991 | Hafelfinger et al. | |
| 5,052,388 A | 10/1991 | Sivula et al. | |
| 5,127,404 A | 7/1992 | Wyborny et al. | |
| 5,201,865 A | 4/1993 | Kuehn | |
| 5,222,493 A | 6/1993 | Sholder | |
| 5,324,310 A | 6/1994 | Greeninger et al. | |
| 5,331,966 A | 7/1994 | Bennett et al. | |
| 5,507,782 A | 4/1996 | Kieval et al. | |
| 5,549,652 A * | 8/1996 | McClure et al. | ............... 607/28 |
| 5,601,615 A | 2/1997 | Markowitz | |
| 5,741,311 A | 4/1998 | Mc Venes et al. | |
| 5,766,230 A * | 6/1998 | Routh et al. | ................... 607/27 |
| 5,861,012 A | 1/1999 | Stroebel | |
| 5,902,325 A * | 5/1999 | Condie et al. | .................. 607/28 |
| 6,058,328 A * | 5/2000 | Levine et al. | .................. 607/14 |
| 6,101,416 A | 8/2000 | Sloman | |
| 6,126,611 A | 10/2000 | Bourgeois et al. | |
| 6,243,606 B1 | 6/2001 | Mann et al. | |
| 6,259,950 B1 | 7/2001 | Mann et al. | |
| 6,263,244 B1 | 7/2001 | Mann et al. | |
| 6,295,471 B1 | 9/2001 | Bornzin et al. | |
| 6,317,633 B1 | 11/2001 | Jorgenson et al. | |
| 6,389,316 B1 * | 5/2002 | Bornzin et al. | ................. 607/28 |
| 6,398,316 B1 | 6/2002 | Mizutani et al. | |
| 6,408,210 B1 | 6/2002 | Bornzin et al. | |

(Continued)

FOREIGN PATENT DOCUMENTS

EP    1 222 942 A2    7/2002

*Primary Examiner*—George R Evanisko
*Assistant Examiner*—Rex Holmes
(74) *Attorney, Agent, or Firm*—Stephen W. Bauer; Reed A. Duthler (57) ABSTRACT

An implantable cardiac stimulation system and method having continuous capture management capabilities are provided. Continuous capture management is realized by continuously monitoring for secondary effects of loss of capture, thereby effectively providing continuous capture management in any heart chamber without encountering the limitations normally associated with evoked response sensing. A pacing threshold search is triggered upon detecting a secondary indicator of loss of capture. Secondary indicators of loss of capture may be lead-related changes, changes related to the occurrence of atrial sensed events, changes related related to the occurrence of ventricular sensed or paced events, and/or changes related to a monitored physiological condition.

11 Claims, 7 Drawing Sheets

U.S. PATENT DOCUMENTS

| | | |
|---|---|---|
| 6,430,448 B1 | 8/2002 | Chitre et al. |
| 6,434,428 B1 | 8/2002 | Sloman et al. |
| 6,438,408 B1 | 8/2002 | Mulligan et al. |
| 6,512,953 B2 * | 1/2003 | Florio et al. .................. 607/28 |
| 6,522,924 B1 | 2/2003 | Meier |
| 7,317,943 B2 * | 1/2008 | Ferek-Petric ................. 607/28 |
| 2001/0031990 A1 * | 10/2001 | Zhang et al. ................... 607/4 |
| 2001/0049543 A1 | 12/2001 | Kroll |
| 2002/0087200 A1 * | 7/2002 | Zhu et al. ..................... 607/27 |
| 2002/0095188 A1 | 7/2002 | Mower |
| 2002/0095190 A1 * | 7/2002 | Bornzin et al. ................ 607/28 |
| 2002/0183798 A1 * | 12/2002 | Vonk ............................ 607/28 |
| 2003/0069611 A1 * | 4/2003 | Levine ......................... 607/27 |
| 2003/0083712 A1 * | 5/2003 | Rueter et al. .................. 607/28 |

* cited by examiner

CARDIAC PACING APPARATUS AND METHOD FOR CONTINUOUS CAPTURE MANAGEMENT

FIELD OF THE INVENTION

The present invention relates generally to the field of implantable cardiac stimulation devices and more particularly to a method for continuous capture management based on monitoring secondary indicators of loss of capture.

BACKGROUND OF THE INVENTION

Cardiac stimulation devices deliver appropriately timed electrical stimulation pulses to a patient's heart to maintain a normal heart rhythm or improve synchronization of heart chambers. Patients having bradycardia, abnormalities of the heart's natural conduction system, a propensity for arrhythmias, cardiac-related breathing disorders, hemodynamic insufficiency, or other cardiac-related conditions may benefit from cardiac pacing therapies delivered in one or more heart chambers.

In order to effectively pace the heart, an electrical impulse delivered to the heart must have sufficient energy to depolarize the myocardial cells. Depolarization of the myocardial cells in response to a pacing pulse is often referred to as "capture." The cardiac electrogram signal evidencing capture, which is a P-wave in the atria or an R-wave in the ventricles, is generally referred to as an "evoked response." The lowest pacing pulse energy that captures the heart may be referred to as the "pacing threshold" or "capture threshold". The amplitude and duration of a pacing pulse are preferably set to produce a pacing pulse energy somewhat greater than the pacing threshold in order to ensure effective cardiac pacing. However, in order to prolong the battery life of the implanted cardiac stimulation device, it is desirable to program the pacing pulse energy to be a minimum value that is considered safely above the pacing threshold.

Pacing threshold, however, can change over time due to tissue encapsulation of the pacing electrodes, lead movement, changes in the patient's clinical condition, changes in medical therapy, or other causes. Therefore, monitoring or detecting pacing threshold changes has diagnostic value as well as therapy delivery implications. A rise in pacing threshold can result in loss of capture and ineffective pacing therapy. Modern pacemakers typically include automatic pacing threshold search algorithms that automatically adjust the pacing pulse energy to ensure pacing pulses remain above the pacing threshold, even if it varies over time. A pacing threshold search may deliver pacing pulses starting at an initially high pulse energy that is greater than the pacing threshold and then progressively decrease the pulse energy until capture is lost. The lowest pulse energy at which capture still occurs is determined as the pacing threshold. In order to reliably determine a pacing threshold, the cardiac pacing device must reliably discriminate between capture and loss of capture.

Capture management is important in the maintenance of effective cardiac pacing. If loss of capture is not recognized by the pacing system, prolonged episodes of subthreshold cardiac pacing may result, during which pacing is ineffective in maintaining a base heart rate, responding to needed increases in heart rate or treating a cardiac-related condition. Pacing-dependent patients may become symptomatic, requiring clinical care and even hospitalization.

One method that has been implemented in commercially available devices for detecting capture is to sense the evoked response following a pacing pulse. Evoked response sensing may be used to verify capture during pacing threshold searches and during normal cardiac pacing operations to ensure that effective pacing is provided. If a loss of capture is detected, as evidenced by the absence of an evoked response following a pacing pulse, a back-up pacing pulse of higher energy may be delivered and a pacing threshold search may be triggered to reset the pacing pulse energy. Pacing systems may provide continuous ventricular capture management by searching for an evoked response following each ventricular pacing pulse. Other systems may provide periodic ventricular capture management by periodically checking for an evoked R-wave or periodically performing a pacing threshold search. Continuous capture management is perceived to be superior to periodic capture verification due to the importance of capture management in maintaining effective pacing therapies.

Sensing of an evoked P-wave for verification of atrial capture, on a periodic or continuous basis, however, is generally more difficult than evoked R-wave sensing because the amplitude of the P-wave is considerably less than the amplitude of the R-wave. Polarization at the electrode-tissue interface causes an afterpotential signal that can saturate sense amplifiers included in the cardiac pacing device and mask an evoked response signal. Typically, a blanking interval is applied to sense amplifiers during and immediately following a pacing pulse to prevent saturation of the amplifiers. The polarization artifact may diminish during the blanking interval, however, it may still interfere with evoked response sensing. Low-polarization electrodes have been proposed for reducing the polarization artifact. See for example U.S. Pat. No. 4,502,492, issued to Bornzin, or U.S. Pat. No. 6,430,448, issued to Chitre, et al.

Various alternative approaches to direct evoked response sensing have been proposed for overcoming limitations due to pacing polarization artifact. Selection of separate sensing electrodes for sensing the evoked response, different than the electrode pair used for delivering the pacing pulse, can reduce or eliminate polarization artifact problems. Sensing a far-field signal related to an evoked response, as opposed to the near-field evoked response signal, or sensing a conducted depolarization away from the pacing site has also been proposed. See for example, U.S. Pat. No. 5,324,310 issued to Greeninger, U.S. Pat. No. 5,222,493 issued to Sholder, U.S. Pat. No. 5,331,966 issued to Bennett et al., U.S. Pat. No. 6,434,428 issued to Sloman, et al., and U.S. Pat. App. No. 20010049543, issued to Kroll. Depending on the associated lead system in use, however, alternative evoked response sensing electrodes may not always be available. With regard to atrial capture management, far-field P-waves may still be difficult to detect because of their relatively low amplitude. Detection of conducted depolarizations as evidence of capture at a pacing site is dependent on intact myocardial conduction pathways.

A method for periodically performing an atrial pacing threshold test is disclosed in U.S. Pat. No. 5,601,615 issued to Markowitz et al, incorporated herein by reference in its entirety. The atrial threshold test regime in patients having intact A-V conduction detects atrial loss of capture by the absence of a detected ventricular depolarization. In a second algorithm, a premature atrial pace is delivered, and the presence of an atrial event at the end of a measured sinus escape interval is declared to be an atrial loss of capture. Other methods for determining an atrial capture threshold are generally disclosed in U.S. Pat. No. 6,263,244 issued to Mann et al., U.S. Pat. No. 6,259,950 issued to Mann et al., U.S. Pat. No. 6,243,606 issued to Mann et al., and U.S. Pat. No. 6,295,471 issued to Bornzin et al.

It is apparent from the above discussion, however, that it is desirable to provide atrial capture management that is continuous rather than relying on periodic pacing threshold searches. Because of the various limitations described above, a cardiac pacing system capable of providing continuous atrial capture management is not presently available. It is desirable, therefore, to provide a cardiac stimulation system capable of effectively monitoring for atrial and/or ventricular capture on a continuous basis.

SUMMARY OF THE INVENTION

The present invention provides a cardiac stimulation system and method having continuous capture management capabilities. Continuous capture management is realized by continuously monitoring for secondary effects of loss of capture, thereby effectively providing continuous capture management in any heart chamber without encountering the limitations normally associated with evoked response sensing. The cardiac stimulation system includes an implantable cardiac stimulation device capable of delivering a cardiac pacing therapy and may include cardioversion and/or defibrillation capabilities. The implantable system further includes an associated lead system for sensing cardiac electrical activity and delivering cardiac stimulation pulses. A control system controls the sensing and stimulation functions of the device and manages the continuous capture management feature provided by the present invention.

Continuous capture management is achieved by monitoring for any of a number of secondary loss of capture (LOC) indicators during pacing therapy delivery. Indicators of LOC may include, but are not limited to: increased number of atrial refractory sensed events; increased number of ventricular paced events; changes in the number of sensed premature ventricular contractions (PVCs); evidence of retrograde conduction; increased number of post-ventricular atrial refractory period (PVARP) extensions; change in pacing lead impedance; change in lead configuration; increased occurrence of mode switching or increased duration of non-atrial tracking episodes; increased detection of cardiac-related disordered breathing episodes; or detection of other secondary physiological changes that may be the result of loss of capture. Detection of a secondary LOC indicator will trigger a pacing threshold search.

In one embodiment, if any of the monitored indicators of loss of capture is detected, a pacing threshold search is performed in both the ventricular and atrial chambers. Preferably, a ventricular pacing threshold search is performed first because ventricular loss of capture is potentially more detrimental to the patient's well being. In alternative embodiments, certain indicators of loss of capture may be more likely to be associated with loss of capture in one chamber than the other. Detection of such indicators will trigger a pacing threshold search in the associated chamber. In yet another embodiment, detection of one or more loss of capture indicators may be more indicative of LOC in one chamber than the other and therefore triggers a pacing threshold search in the appropriate chamber first and the other chamber second.

Continuous monitoring of secondary LOC indicators advantageously provides the effect of continuous capture management, which can improve the performance of a cardiac stimulation device in delivering effective pacing therapies. Furthermore, if LOC is not verified during a pacing threshold search following detection of a secondary LOC indicator, the indicator may be caused by other changes in device performance or the patient's clinical condition. Such changes may warrant further diagnosis or operating parameter or therapy adjustments. Thus, by verifying that a loss of capture indicator is or is not the result of a pacing threshold change, device diagnostics and therapy responses may be improved.

DETAILED DESCRIPTION OF THE INVENTION

As indicated above, the present invention is directed toward achieving continuous capture management in atrial and/or ventricular heart chambers. As such, the benefits of continuous capture management provided according to the present invention may be realized in single, dual, or multi-chamber cardiac stimulation devices, which are capable of delivering a cardiac pacing therapy. The term "cardiac pacing therapy" is used herein to refer to any cardiac stimulation therapy that employs relatively low-energy stimulation pulses to depolarize the myocardial tissue to achieve a therapeutic effect. Cardiac pacing therapies may include but are not limited to, bradycardia pacing, cardiac resynchronization therapy, extra systolic stimulation therapies, overdrive pacing for treating or preventing arrhythmias or cardiac-related disordered breathing, and anti-tachycardia pacing therapies.

Figure 1:
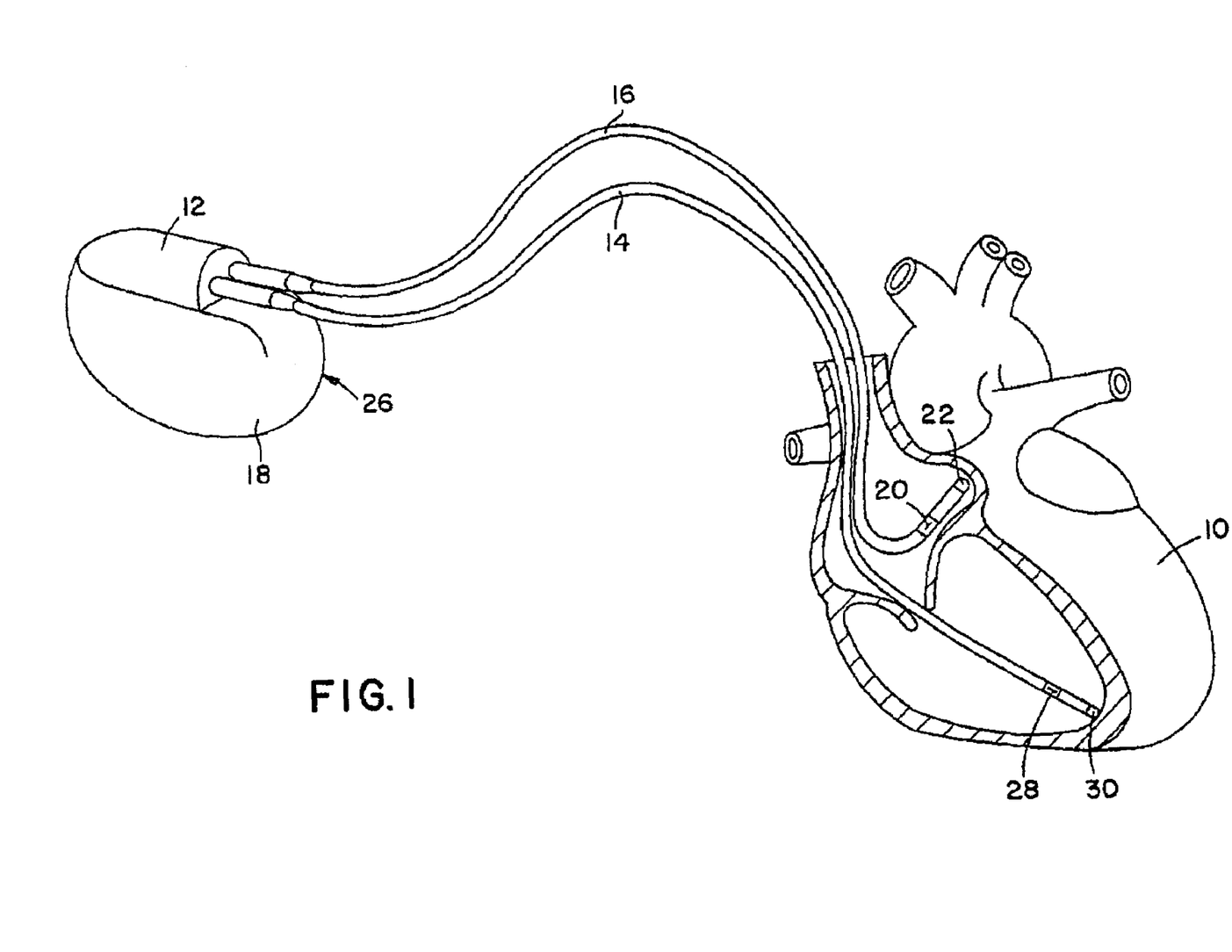
FIG. 1 is an illustration of an exemplary cardiac stimulation device in which the present invention may be usefully practiced.

FIG. 1 is an illustration of an exemplary cardiac stimulation device in which the present invention may be usefully practiced. FIG. 1 illustrates the external configuration of a dual chamber cardiac stimulation device 26, which is provided with a hermetically sealed enclosure 18, typically fabricated of biocompatible metal such as titanium. Mounted to the top of the enclosure 18 is a connector block assembly 12, which receives electrical connectors located on the proximal ends of leads 14 and 16. The combination of the leads 14 and 16 and the device 26 constitute an implantable cardiac stimulation system. FIGS. 1 through 3 are described in U.S. Pat. No. 5,507,782, issued to Kieval et al., which is hereby incorporated by reference.

Lead 16 is an atrial bipolar cardiac stimulation and sensing lead, carrying two electrodes 20 and 22. Electrodes 20 and 22 are used both to sense atrial depolarizations (P-waves) and to deliver atrial stimulation pulses. Atrial stimulation pulses may be delivered between electrodes 20 and 22 in a bipolar mode or between electrode 22 and the housing 18 of device 26 in a unipolar mode. Sensing of P-waves may occur between electrode 20 and electrode 22 in a bipolar sensing mode or between either of electrode 20 and 22 and the housing 18 of device 26 in a unipolar sensing mode.

Similarly, lead 14 represents a ventricular bipolar cardiac stimulation and sensing lead, carrying two electrodes 28 and 30. As discussed above in conjunction with atrial lead 16, electrodes 28 and 30 are used to sense and stimulate the ventricle. Bipolar ventricular stimulation may be accomplished between electrodes 30 and 28 or unipolar ventricular stimulation may be accomplished between electrode 30 and the conductive housing 18 of device 26. Sensing of ventricular depolarizations (R-waves) may be accomplished between electrodes 30 and 28 in a bipolar sensing mode or between either of electrodes 30 and 28 and the housing 18 of device 26 in a unipolar sensing mode.

As discussed below, the specific embodiment of device 26 disclosed preferably operates in a DDD or DDDR pacing mode, wherein pacing pulses are delivered to both atrium and ventricle and wherein sensed atrial and ventricular depolarizations are both effective to inhibit delivery of the next scheduled pacing pulse in the chamber in which they are detected. The atrial and ventricular continuous capture management afforded by the present invention may be optimally practiced in a device operating in the DDD, DDI, DVI, DDDR, DVIR and DDIR pacing modes. However, the continuous capture management methods practiced according to the present invention can also be beneficial in various single chamber or multi-chamber pacing modes.

Figure 2:
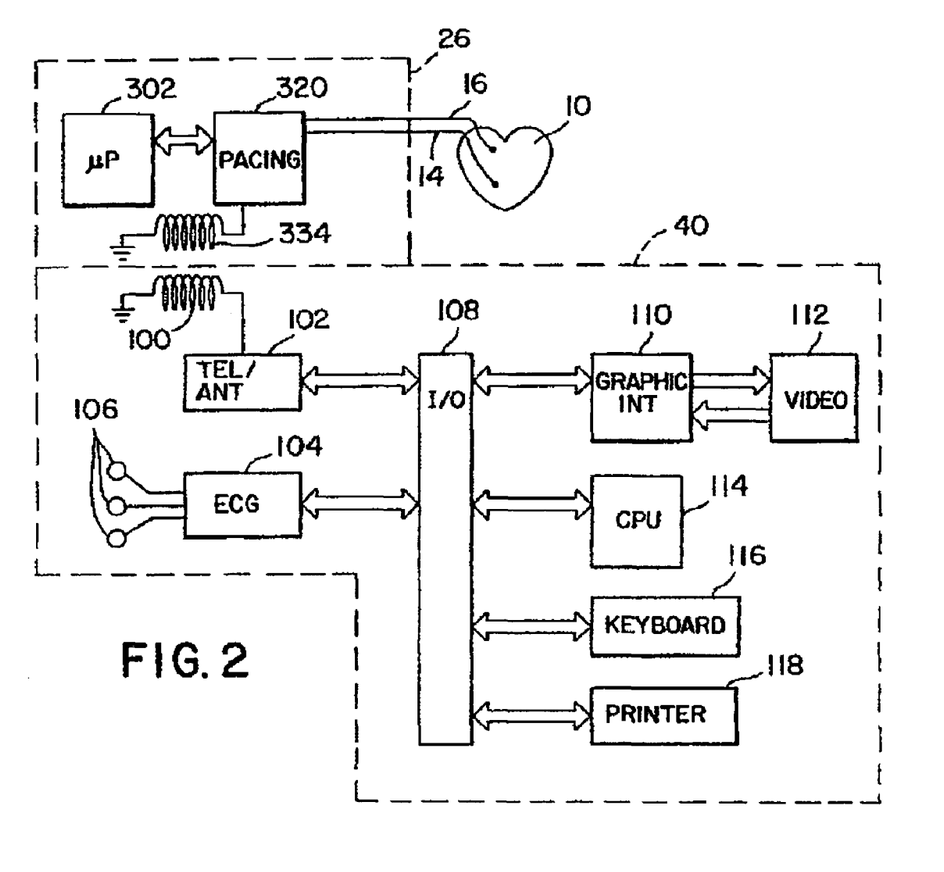
FIG. 2 illustrates the cardiac stimulation device of FIG. 1 in block diagram form.

FIG. 2 illustrates the cardiac stimulation device 26 in block diagram form, coupled to a human heart 10 through the leads 14, 16, in conjunction with an external programmer 40 corresponding to those typically employed to program modern, multi-programmable implantable cardiac stimulation devices. Within the housing of the device 26 are located the pacing circuitry 320, which includes circuitry performing all of the basic timing, stimulation and sensing functions of a DDD or DDDR cardiac pacemaker, and a microcomputer circuit 302, which controls the timing intervals provided by the pacing circuitry 320. Pacing circuitry 320 also includes a bi-directional telemetry circuit coupled to an antenna 334, allowing transmission of information from external programmer 40 into implantable device 26 to modify its parameters and allowing transmission of information from device 26 to the external programmer 40, again generally corresponding to telemetry and programming systems presently existing in commercially available multi-programmable implantable cardiac stimulation devices.

The programmer 40 also includes a telemetry antenna 100 coupled to a telemetry/antenna driver circuit 102 which serves to demodulate telemetry signals received from antenna 334 of device 26, and to apply them in parallel or serial digital format to input/output (I/O) unit 108. The telemetry signals in turn may be applied to a video monitor 112, via graphic interface 110, and/or provided to central processing unit 114 and/or printer 118. Microprocessor 114 controls the operation of the programmer 40 and is responsive to physician entered commands via keyboard 116, for controlling programming signals sent to device 26 and operation of the video display 112 and printer 118. Also illustrated in FIG. 2 is an ECG interface 104 coupled to three ECG electrodes 106 which are intended to be placed upon the patient's body. ECG interface 104 provides sensed electrocardiograms to input/output device 108, where they in turn may be provided to the video display 112, the central processing unit 114 or the printer 118.

Figure 3:
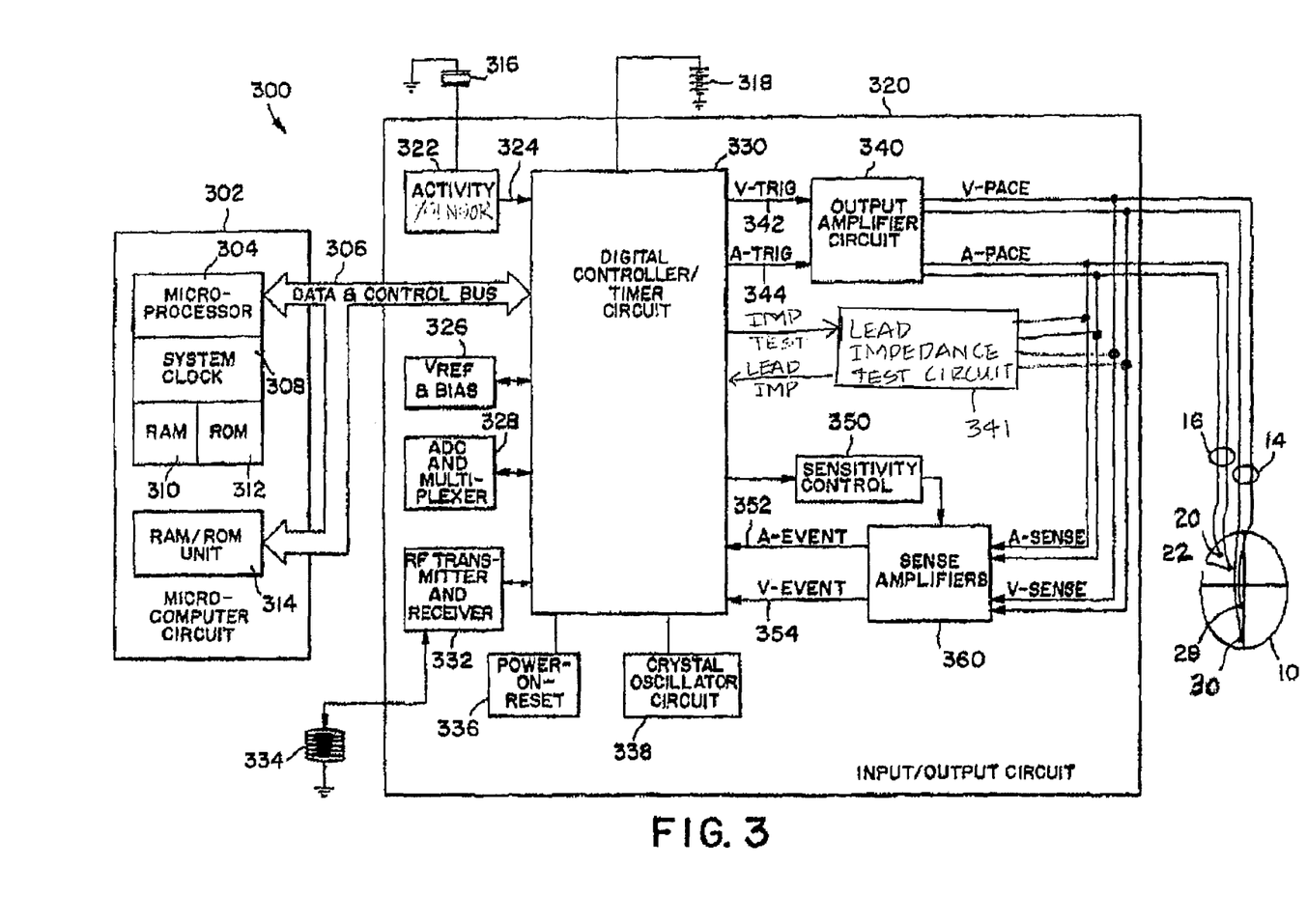
FIG. 3 is a more detailed functional block diagram of the cardiac stimulation device illustrated in FIGS. 1 and 2.

FIG. 3 is a more detailed functional block diagram of the cardiac stimulation device illustrated in FIGS. 1 and 2. The device circuit 300 is located within housing 18 of device 26 as illustrated in FIG. 1. The bipolar leads 14 and 16 are illustrated schematically as coupled directly to the input/output circuit 320. However, in the actual implantable device they would, of course, be coupled by means of removable electrical connectors inserted in the connector block 12 illustrated in FIG. 1.

Circuit 300 is divided generally into a microcomputer circuit 302 and a pacing circuit 320. An output amplifier circuit 340 includes a ventricular pulse generator circuit coupled to the ventricle of the heart 10 by means of electrodes 28 and 30 on lead 16 as well as an atrial pulse generator circuit coupled to the atrium of heart 10 by means of atrial electrodes 20 and 22, located on lead 14. Similarly, sense amplifier circuit 360 includes atrial and ventricular sense amplifiers coupled to the atrium and ventricle, respectively, by means of leads 14 and 16. The output circuit 340 and sense amplifier circuit 360 may contain pulse generators and sense amplifiers, respectively, corresponding to any of those presently employed in commercially available cardiac pacemakers.

Sensed atrial depolarizations (or P-waves) that are detected by the atrial sense amplifier, in response to an atrial signal received from atrial lead 14 exceeding an atrial P-wave sensing threshold, are communicated to the digital controller/timer circuit 330 on A-event line 352. Similarly, ventricular depolarizations (or R-waves) that are detected by the ventricular sense amplifier, in response to a ventricular signal received from ventricular lead 16 exceeding a ventricular R-wave sensing threshold, are communicated to the digital controller/timer circuit 330 on V-event line 354. In order to trigger generation of a ventricular pacing pulse, digital controller/timer circuit 330 generates a trigger signal on V-trig line 342. Similarly, in order to trigger an atrial pacing pulse, digital controller/timer circuit 330 generates a trigger pulse on A-trig line 344.

Control of timing and other functions within the pacing circuit 320 is provided by digital controller/timer circuit 330, which includes a set of timers and associated logic. Digital controller/timer circuit 330 defines the basic pacing or escape intervals controlling the timing of atrial and ventricular pacing pulse delivery. An A-A escape interval is initiated on atrial sense (A-event) or atrial pace (A-pace) events. An atrial pacing pulse (A-pace) is triggered at the expiration of the A-A escape interval. A V-V escape interval is initiated on ventricular sense (V-event) or pace (V-pace) events, and a ventricular pulse pacing (V-pace) is triggered upon the expiration thereof. Digital controller/timer circuit 330 also defines A-V intervals that commence following a sensed A-event or a delivered A-pace, and upon the expiration thereof a ventricular pacing pulse is triggered. The specific values of the escape intervals defined by timer circuit 330 are controlled by the microcomputer circuit 302 by means of data and control bus 306 according to programmed parameter values and operating modes.

Digital controller/timer circuit 330 also controls sensitivity settings of the sense amplifiers 360 by means of sensitivity control 350 and defines time intervals for controlling operation of the atrial and ventricular sense amplifiers in sense amplifier circuit 360. Typically, digital controller/timer circuit 330 defines an atrial blanking interval and a ventricular blanking interval following delivery of an A-pace pulse, during which atrial sensing and ventricular sensing are disabled. Following ventricular pacing pulse delivery, a ventricular blanking interval and a post-ventricular atrial blanking (PVAB) interval are applied, during which ventricular and atrial sensing are disabled.

Digital controller/timer circuit 330 also defines a number of refractory periods during which sensing is enabled but any sensed events are labeled as refractory sensed events, which may be categorized and responded to differently than non-refractory sensed events. The various refractory periods are intended to prevent inappropriate signals such as retrograde P-waves, far-field R-waves or noise from resetting the atrial or A-V escape intervals. Refractory sensed events are therefore not used to restart certain timing intervals controlled by digital controller/timer circuit 330. Refractory periods generally begin with a blanking period followed by a period during which events may be sensed as refractory events. An atrial refractory period (ARP), which includes the atrial blanking period, is applied following an atrial pacing pulse during which atrial sensed event is ignored for the purpose of resetting an atrial escape interval.

Digital controller/timer circuit 330 also defines a ventricular refractory period (VRP) following either a V-event or V-pace. A post-ventricular atrial refractory period (PVARP), which includes the post-ventricular atrial blanking period, typically follows a paced, sensed or refractory sensed ventricular event. The PVARP is primarily intended to prevent resetting of the atrial escape interval due to sensing of retrograde P-waves, which might promote pacemaker-mediated tachycardia (PMT). The durations of the various refractory periods may also be selected as a programmable parameter stored in the microcomputer 302.

The PVARP may be automatically extended in response to sensing certain events such as premature ventricular contractions (PVCs) or PMT. A PVC is defined as any ventricular sensed event (refractory or non-refractory) that follows a ventricular event, which may be a ventricular pacing pulse or refractory or non-refractory sensed event, without an intervening atrial paced, refractory or non-refractory sensed event. In response to PVC detection, the PVARP is extended to prevent inhibition of atrial pacing by sensed retrograde P-waves generated by PVCs. PMT is detected by device 26 when a predetermined number of atrial sensed events occur within a short interval, for example within 400 ms, of a ventricular pacing pulse. In response to PMT detection, the PVARP is extended to prevent tracking of retrograde P-waves.

In the embodiment illustrated in FIG. 3, device 26 is provided with a sensor 316, which may be a piezoelectric sensor intended to monitor patient activity, in order to allow provision of rate responsive pacing, such that the defined pacing rate (A-A escape interval or V-V escape interval) increases with increased levels of sensed activity. Sensor 316 generates electrical signals in response to sensed physical activity which are processed by activity/sensor circuit 322 and provided to digital controller/timer circuit 330 on signal line 324. Activity/sensor circuit 322 and associated sensor 316 may correspond to the circuitry disclosed in U.S. Pat. No. 5,052,388, issued to Sivula et al., and U.S. Pat. No. 4,428,378, issued to Anderson et al. incorporated herein by reference in their entireties. Similarly, the present invention may be practiced in conjunction with alternate types of physiological sensors such as oxygen sensors, pressure sensors, pH sensors and respiration sensors, all known for use in providing rate responsive pacing capabilities. As stated above, the present invention may also be practiced in non-rate responsive pacemakers.

In alternative embodiments, a physiological sensor 316 and corresponding activity/sensor circuit 322 may alternatively be used for monitoring cardiac hemodynamic performance, myocardial contractile performance, a metabolic state or other physiological condition. Physiological sensors known for use in conjunction with implanted devices may include blood pressure sensors, oxygen saturation sensors, pH sensors, temperature sensors, blood flow sensors, acoustical sensors, accelerometers, impedance sensors and so forth. Signals from such sensors may be processed for determining a need for therapy delivery or therapy adjustment as a physiological condition or metabolic need changes.

Data transmission to and from the external programmer 40 illustrated in FIG. 2 is accomplished by means of the telemetry antenna 334 and an associated RF transmitter and receiver 332, which serves both to demodulate received downlink telemetry and to transmit uplink telemetry. For example, circuitry for demodulating and decoding downlink telemetry may correspond to that disclosed in U.S. Pat. No. 4,556,063 issued to Thompson et al. and U.S. Pat. No. 4,257,423 issued to McDonald et al., while uplink telemetry functions may be provided according to U.S. Pat. No. 5,127,404 issued to Wyborny et al. and U.S. Pat. No. 4,374,382 issued to Markowitz. Uplink telemetry capabilities will typically include the ability to transmit stored digital information as well as real time or stored EGMs of atrial and/or ventricular electrical activity (according to the teaching of the above-cited Wyborny patent), as well as transmission of Marker Channel pulses indicating the occurrence of sensed and paced depolarizations in the atrium and ventricle, as disclosed in the cited Markowitz '382 patent.

In addition, in the context of the present invention, stimulation threshold data from pacing threshold searches may be stored in the RAM 310 or the RAM/ROM unit 314 of microcomputer 302 for later telemetry out on command of the programmer 40. This data may be encoded in digital form and transmitted via RF transmitter 332 and antenna 334 to the external programmer 40 for display and/or analysis in the form of atrial and ventricular strength-duration curves as described in the previously-incorporated '615 patent issued to Markowitz et al. Data pertaining to detected secondary LOC indicators which trigger pacing threshold searches during the continuous capture management, in accordance with the present invention, may also be stored in RAM 310 for later telemetry out for diagnostic and therapy management purposes.

Crystal oscillator circuit 338 provides the basic timing clock for the pacing circuit 320, while battery 318 provides power. Power-on-reset circuit 336 responds to initial connection of the circuit to the battery for defining an initial operating condition and similarly, resets the operative state of the device in response to detection of a low battery condition. Reference mode circuit 326 generates stable voltage reference and currents for the analog circuits within the pacing circuit 320, while analog to digital converter (ADC) and multiplexer circuit 328 digitizes analog signals and voltage to provide real time telemetry of cardiac signals from sense amplifiers 360, for uplink transmission via RF transmitter and receiver circuit 332. Voltage reference and bias circuit 326, ADC and multiplexer 328, power-on-reset circuit 336 and crystal oscillator circuit 338 may correspond to any of those presently used in currently available implantable cardiac stimulation devices.

Microcomputer 302 controls the operational functions of digital controller/timer 330, specifying which timing intervals are employed, and controlling the duration of the various timing intervals, via data and control bus 306. Microcomputer 302 contains a microprocessor 304 and associated system clock 308 and on-processor RAM and ROM chips 310 and 312, respectively. In addition, microcomputer circuit 302 includes a separate RAM/ROM chip 314 to provide additional memory capacity. Microprocessor 304 is interrupt driven, operating in a reduced power consumption mode normally, and awakened in response to defined interrupt events, which may include the A-trig, V-trig, A-event and V-event signals.

As described above, if the device 26 is programmed to operate in a rate responsive mode, the patient's activity level is monitored periodically and the escape interval is adjusted proportionally. A timed interrupt, e.g., every two seconds, may be provided in order to allow the microprocessor 304 to analyze the output of the activity circuit 322 and update the basic escape interval (A-A or V-V). The microprocessor 304 may also define variable A-V intervals and variable refractory periods, which vary with the escape interval established in response to patient activity. For example, the microprocessor 304 may specify a variable rate adaptive decrement interval to be subtracted from the defined A-V intervals when the heart rate (paced or sensed) is above a defined resting or base rate. Similarly microprocessor 304 may define atrial and ventricular refractory periods which decrease in duration in relation to an increase in sensed or paced heart rate above the base rate.

Device 26 may further include lead impedance measuring circuitry 341 coupled to leads 14 and 16 for monitoring changes in lead impedance. Implantable medical devices capable of measuring and monitoring changes in lead impedance are generally disclosed in U.S. Pat. No. 5,201,865 issued to Kuehn, U.S. Pat. No. 5,741,311 issued to McVenes et al., and U.S. Pat. No. 6,317,633 issued to Jorgenson et al., all of which are incorporated herein by reference in their entirety.

The illustrated device block diagram of FIG. 3 is merely exemplary, and corresponds to the general functional organization of a typical multi-programmable microprocessor controlled DDD(R) cardiac pacemaker. It is believed that the present invention is readily practiced in the context of such a device, and that the present invention can therefore readily be practiced using the basic hardware of existing microprocessor controlled dual chamber pacemakers, as presently available, with the invention implemented primarily by means of modifications to the software stored in the ROM 312 of the microcomputer circuit 302. However, the present invention may also be usefully practiced by means of a full custom integrated circuit, for example, a circuit taking the form of a state machine as set forth in the above-cited Betzold et al. patent, in which a state counter serves to control an arithmetic logic unit to perform calculations according to a prescribed sequence of counter controlled steps. As such, the present invention should not be understood to be limited to a cardiac stimulation device having an architecture as illustrated in FIG. 3, and a circuit architecture as illustrated in FIG. 3 is not believed to be a prerequisite to enjoying the benefits of the present invention.

Furthermore, while a particular dual-chamber implantable cardiac stimulation device and lead system is shown in FIGS. 1 through 3, the present invention may be usefully practiced in other types of cardiac stimulation devices such as any single, dual or multi-chamber cardiac stimulation device capable of providing cardiac pacing therapies, which may include bradycardia pacing, cardiac resynchronization therapies, atrial overdrive pacing for treating sleep apnea or other cardiac-related breathing disorders, and/or extra systolic stimulation therapies, and may further include anti-tachycardia pacing therapies, and/or higher-voltage stimulation therapies for cardioversion and defibrillation. As such, other types of lead systems may be substituted for the particular lead system shown in FIG. 1 according to the type of cardiac stimulation device implanted. Unipolar, bipolar, and/or multipolar leads provided with tip, ring, and/or coil electrodes may be used. A lead system may be used to position electrodes within the heart or external to the heart such as epicardial or subcutaneous placements.

Figure 4:
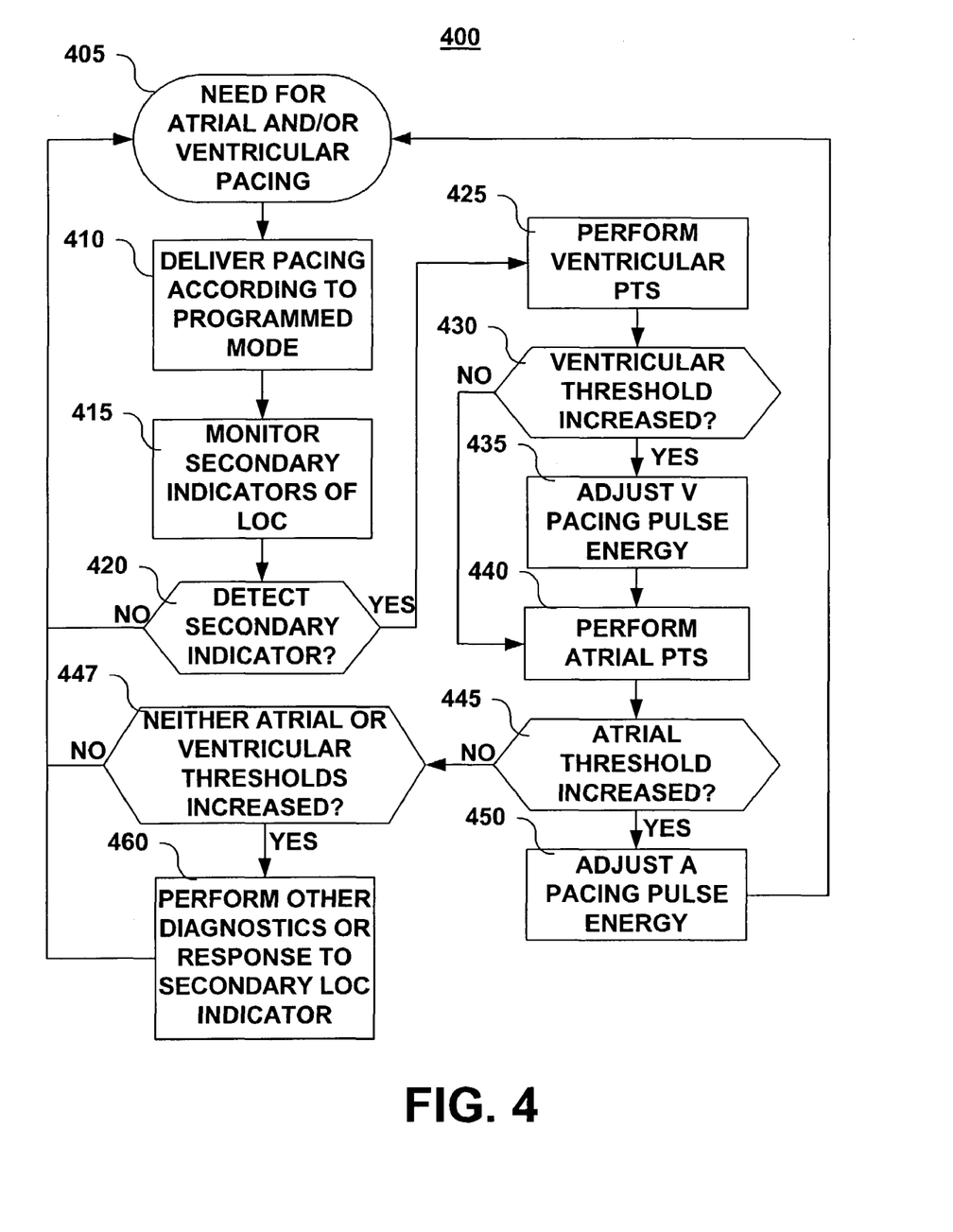
FIG. 4 is a flow chart providing an overview of a method for achieving continuous capture management according to the present invention.

FIG. 4 is a flow chart providing an overview of a method for achieving continuous capture management according to the present invention. Continuous capture management is realized by continuously monitoring for secondary indicators of loss of capture whenever the implantable cardiac stimulation device is delivering atrial and/or ventricular pacing pulses. As such, method 400 of FIG. 4 begins at initiation step 405 when the need for atrial and/or ventricular pacing arises according to the current device operating mode. Atrial and/or ventricular pacing pulses are delivered at step 410. Throughout an atrial and/or ventricular pacing episode, the cardiac stimulation device, through a programmed sensing module, monitors for secondary indicators of loss of capture (LOC) at step 415.

As will be described in greater detail below, secondary LOC indicators may relate only to atrial loss of capture, only to ventricular loss of capture or either atrial or ventricular loss of capture. Monitoring for secondary indicators of LOC may include monitoring the occurrences of atrial refractory sensed signals, ventricular paced and/or sensed events, the results of other device diagnostic functions, or changes in device operating mode and/or other physiological signals.

If a secondary indicator of LOC is detected, as determined at decision step 420 by for example, an programmed analysis module, the cardiac stimulation device will perform a pacing threshold search (PTS) in order to determine if the occurrence of the secondary LOC indicator is indeed the result of LOC. In one embodiment, both ventricular and atrial pacing threshold searches are performed in response to detecting any secondary indicator of LOC. Preferably, a ventricular PTS is performed first, and an atrial PTS is performed second because of the relatively greater importance of maintaining effective ventricular pacing in pacemaker-dependent patients.

In an alternative embodiment, a ventricular PTS may be performed first, and, if the ventricular pacing threshold has increased, ventricular LOC is presumed the cause of the secondary indicator of LOC. An atrial PTS is not immediately performed unless a secondary LOC indicator continues to be detected. In yet another embodiment, a ventricular or atrial PTS may be performed first depending on the nature of the secondary LOC indicator. If the secondary LOC indicator is most closely related to an atrial LOC, an atrial PTS may be performed first, and a ventricular PTS performed second. If the atrial pacing threshold is changed, a ventricular PTS may not be performed immediately unless a secondary indicator of LOC continues to be detected after adjusting the atrial pacing pulse energy.

A PTS is preferably performed according to algorithms disclosed in the above-cited '615 patent to Markowitz. Generally, a premature test pacing pulse is inserted during an episode of sensed, sinus events. If an event is sensed prior to the expiration of the next escape interval, the test pulse did not capture. A sequence of premature test pacing pulses at varying pulse energies are delivered during a sustained episode of intrinsic sinus rhythm to determine the lowest pacing pulse energy that interrupts the sensed events.

If a sustained sinus rhythm is not present and the patient is known to have intact atrial-ventricular conduction, an alternative PTS algorithm may be performed. In an alternative atrial PTS algorithm, atrial test pacing pulses are delivered at a test escape interval followed by a test A-V interval. Capture is confirmed by the presence of a ventricular sensed event during the test A-V interval. A sequence of atrial test pacing pulses at varying pulse energies are used to determine the lowest pulse energy at which capture occurs, as confirmed by sensing the conducted depolarization in the ventricle.

An alternative ventricular PTS may be performed by delivering a ventricular test pacing pulse at a shortened test A-V interval. If a ventricular refractory sense occurs following the test pulse, the test pulse did not capture. A sequence of test pulses is delivered at varying pulse energies to determine the lowest pulse energy at which capture occurs, as confirmed by the absence of a ventricular refractory sense following the test pulse. However, it is recognized that other methods known in the art for performing atrial or ventricular pacing threshold searches may be successfully employed for re-determining a pacing threshold following detection of a secondary LOC indicator.

In the embodiment shown in FIG. 4, both a ventricular PTS and atrial PTS are performed in response to the detection of a secondary LOC indicator. At step 425, a ventricular PTS is performed first because of the more serious nature of ventricular LOC. If the ventricular pacing threshold has increased, as determined at decision step 430, the ventricular pacing pulse energy is adjusted accordingly at step 435. Method 400 proceeds to step 440 to perform an atrial PTS. If the ventricular pacing threshold has not increased (decision step 430), method 400 proceeds directly to step 440 to perform an atrial PTS. It is recognized that if the ventricular pacing threshold has decreased, as determined by the PTS, the ventricular pacing pulse energy may be adjusted to a lower energy as is customary in cardiac stimulation devices.

At decision step 445, method 400 determines if the atrial pacing threshold has increased based on the atrial PTS performed at step 440. If so, the atrial (A) pacing pulse energy is appropriately increased at step 450. The secondary indicator of LOC is concluded to be the result of the ventricular and/or atrial pacing threshold increase. Method 400 returns to step 405 and continues to deliver atrial and/or ventricular pacing as needed and monitoring for secondary indicators of LOC.

If the atrial pacing threshold has not increased, as determined at decision step 445, method 400 proceeds to decision step 447. If either ventricular or atrial pacing threshold has increased (a negative result to the decision at step 447), method 400 concludes that ventricular and/or atrial LOC was the cause of the secondary indicator of LOC. Method 400 returns to step 405 to continue cardiac pacing as needed and monitoring for secondary LOC indicators.

If, however, the results of the ventricular and atrial PTSs indicate that neither the ventricular or atrial pacing thresholds have increased (an affirmative result to decision step 447), method 400 concludes that LOC has not occurred and is not the cause of the secondary indicator of LOC. Method 400 may proceed to optional step 460 to perform additional diagnostics or provide another response to the change associated with the detected secondary LOC indicator. Method 400 may then return to step 405 to await the next pacing episode. Data supporting the detection of a secondary LOC indicator may be stored in memory at step 460 for later uplinking to an external device for review by a clinician. Such data may be useful for diagnostic purposes or in selecting and programming device operating parameters.

Secondary indicators of LOC may also occur when other device operating parameters, other than pacing pulse energy, are no longer appropriate due to changes relating to the electrode-tissue interface or physiological changes associated with disease state, medical therapies, etc. Thus other responses to secondary LOC indicators that may be taken at step 460 when LOC is ruled out as the cause of the secondary indicator may include adjusting a sensitivity setting, adjusting refractory or blanking periods, adjusting a pacing mode, or triggering the delivery or withholding of cardiac stimulation or other therapy.

Figure 5:
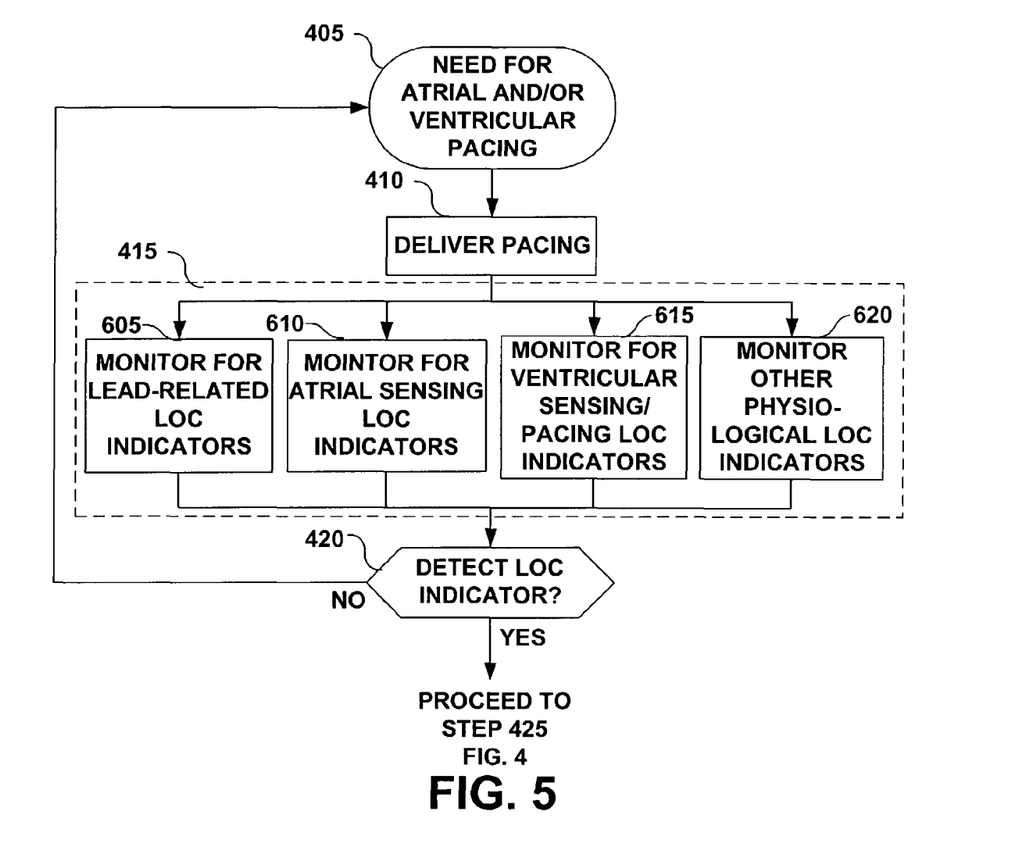
FIG. 5 is a flow chart providing additional details regarding steps included in monitoring for secondary indicators of loss of capture (LOC) in the method of FIG. 4.

FIG. 5 is a flow chart providing additional details regarding steps included in monitoring for secondary indicators of loss of capture. FIGS. 6A through 6D are diagrams showing in greater detail the secondary LOC indicator monitoring methods included in one embodiment of the method of FIG. 5. Identically-numbered steps shown in FIG. 5 correspond to those steps shown in FIG. 4. In FIG. 5, step 415 for monitoring for secondary LOC indicators is shown to include a number of steps 605, 610, 615, and 620 for monitoring for different types of secondary indicators of LOC.

At step 605, secondary indicators based on lead-related changes are monitored. As shown in greater detail in FIG. 6A, lead related changes that can be detected as secondary indicators of LOC may include, but are not limited to, changes in atrial or ventricular lead impedance (step 625 of FIG. 6A) and lead configuration changes (step 630 of FIG. 6A). A change in lead impedance may indicate lead dislodgment or shifting, lead fracture, insulation breach or other change affecting the electrical coupling between the tissue interface and electrodes and implanted device. Such changes may result in an increase in pacing threshold resulting in a loss of capture.

Figure 6A:
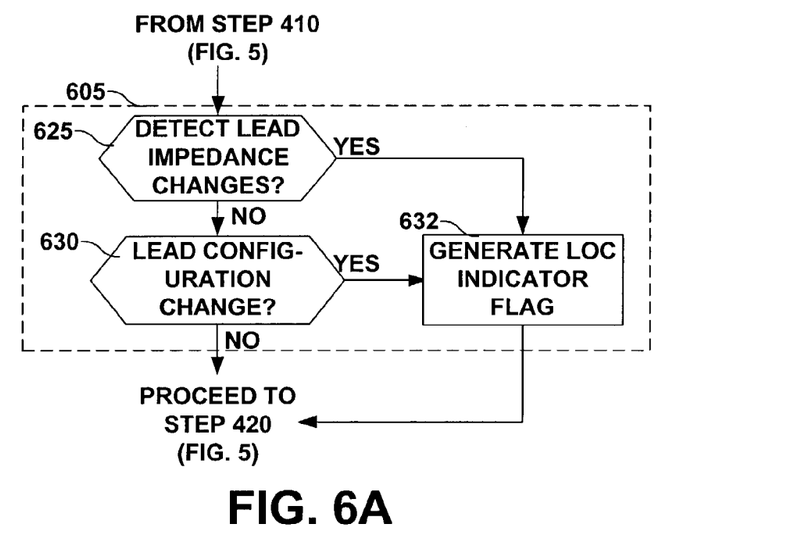
FIGS. 6A through 6D are diagrams showing in greater detail the secondary LOC indicator monitoring methods included in one embodiment of the method of FIG. 4.

Lead configuration changes may be made automatically by the cardiac stimulation device in response to lead impedance monitoring. Lead configuration changes may be made according to the above-referenced '311 patent and as generally described in U.S. Pat. No. 5,003,975 issued to Hafelfinger et al., incorporated herein by reference in its entirety. If a lead configuration change has occurred, the currently programmed pacing pulse energy may be below the pacing threshold for the new lead configuration and/or the pacing threshold may be increased. Other types of lead-related changes may be used as secondary LOC indicators such as lead-related issues detected by a lead status monitor as generally described in the above-cited Jorgenson patent.

If a lead-related indicator of possible LOC is detected as determined at decision steps 625 and/or 630, a LOC indicator flag is generated at step 632. At decision step 420 of FIG. 5, the LOC indicator is detected such that ventricular and atrial PTSs will be performed, as described previously in conjunction with FIG. 4, to verify that the current atrial and ventricular pacing pulse energies are set appropriately above the atrial and ventricular pacing thresholds, respectively. In one embodiment, if a lead-related LOC indicator pertains only to an atrial lead, only an atrial PTS may be performed. Likewise, if a lead-related LOC indicator pertains only to a ventricular lead, only a ventricular PTS may be performed.

Figure 6B:
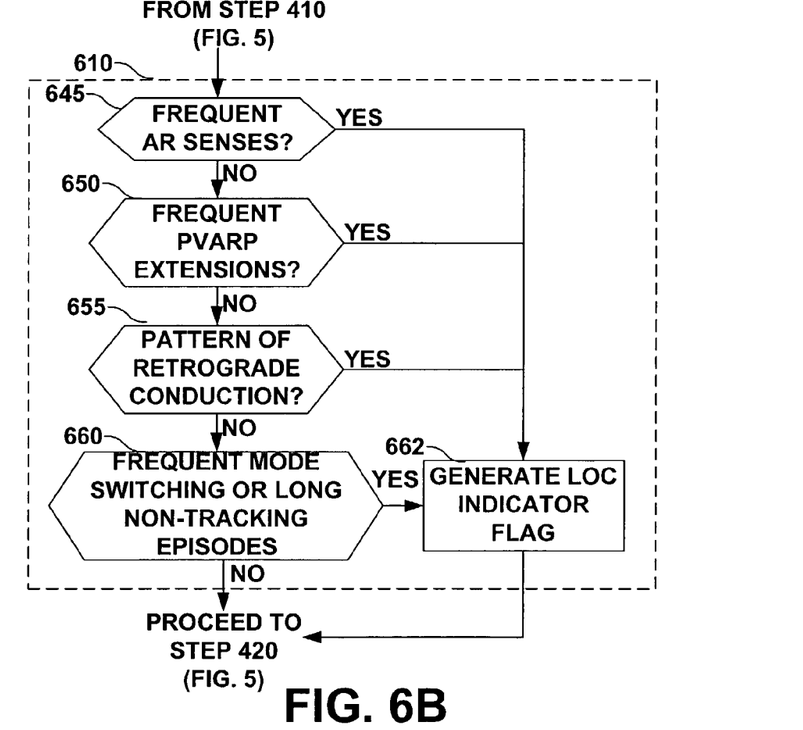

At step 610 of FIG. 5, secondary LOC indicators relating to changes in atrial sensed events are monitored. As shown in FIG. 6B, changes relating to atrial sensed events that can be included in monitoring for secondary LOC indicators may be, but are not limited to: an increased frequency of atrial refractory sensed events (step 645); a detected pattern of retrograde conduction (step 650); an increased frequency of PVARP extensions (step 655); and/or frequent mode switching (step 660).

If atrial LOC is occurring during an episode of atrial pacing, the underlying intrinsic atrial rate, asynchronous with the atrial pacing rate, may appear as atrial refractory sensed events. Thus, an increase in the frequency of atrial refractory sensed events may be detected at step 645, causing a LOC indicator flag to be generated at step 662.

Atrial refractory sensed events may also be the result of retrograde conduction. A ventricular evoked response to a ventricular pacing pulse delivered at a programmed A-V interval may be conducted retrograde to the atria if the preceding atrial pacing pulse did not capture the atria, which would otherwise cause the atrial tissue to be in refractory during ventricular pacing pulse delivery. Patterns of retrograde conduction may be recognized based on the timing relation between atrial refractory sensed events and ventricular events. For example, an atrial refractory sensed event occurring within a given interval following a ventricular paced or sensed event may be determined to be a retrograde P-wave. If an increased frequency in retrograde conductions is detected at step 650, a LOC indicator flag is generated at step 662.

An increase in the number of PVARP extensions detected at step 655 may also cause a LOC indicator flag to be generated at step 662. The PVARP is extended upon detection of PVCs or PMT, as noted previously. An increase in the number of detected PVCs causing PVARP extension may indicate an underlying intrinsic ventricular or atrial rate may be present due to ventricular or atrial LOC. Likewise, detected PMT may be associated with atrial loss of capture resulting in retrograde P-waves as described above. Thus, frequent PVARP extensions may be a secondary indicator of LOC.

When mode switching is enabled, if the sensed atrial rate exceeds a maximum atrial tracking rate, the pacing mode will switch to a non-atrial tracking mode. Mode switching is designed to prevent atrial tracking of paroxysmal atrial tachycardias during DDDR, DDD, and VDD pacing modes. Overdrive atrial pacing may be provided to suppress atrial tachycardia or fibrillation. If the atrial pacing rate exceeds a maximum tracking rate, the pacing mode will also switch to a non-atrial tracking mode. Increased occurrences of mode switching between atrial tracking and non-tracking modes, or relatively long episodes of non-atrial tracking modes, may occur when an atrial rate exceeding the maximum tracking rate is detected. However, this high rate may be detected when an increased incidence of atrial refractory senses occur as a result of atrial or ventricular LOC or intermittent LOC. If frequent mode switching or relatively long episodes of non-atrial tracking modes are detected at step 660, a LOC indicator flag is generated at step 662.

While steps 645 through 660 are shown in a sequential order in FIG. 6B, it is recognized that monitoring for various atrial sensing-related changes may be performed simultaneously such that if any of the atrial sensing-related changes occurs, a LOC indicator flag is generated, triggering ventricular and atrial PTSs upon the LOC indicator detection made at step 420 of FIG. 5.

Figure 6C:
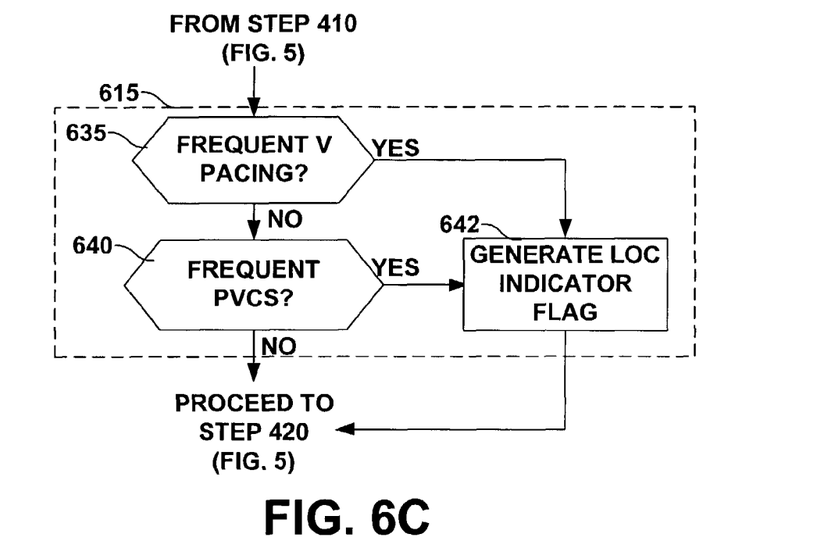

At step 615 of FIG. 5, secondary LOC indicators relating to the occurrence of ventricular sensed and paced events are monitored. As shown in FIG. 6C, ventricular-related events that can indicate LOC may include, but are not limited to: increased frequency of ventricular pacing (step 635) and/or increased frequency of premature ventricular contraction (PVC) detections (step 640).

If atrial LOC has occurred, ventricular pacing may be triggered because the ventricles are not depolarized by a conducted evoked response from the atrium. Therefore, if there is an increased incidence of ventricular pacing detected at step 645 during atrial pacing in patients previously known to have intact A-V conduction, a LOC indicator flag may be generated at step 642.

PVCs may be detected as any refractory or non-refractory ventricular sensed event that follows a ventricular sensed (refractory or non-refractory) or paced event without an intervening atrial event (paced, refractory or non-refractory sensed). An increase in the number of PVCs may indicate an underlying intrinsic ventricular or atrial rate may be present due to ventricular or atrial LOC. An increase in the number of PVCs detected at step 640 may therefore generate a LOC indicator flag at step 642, triggering both ventricular and atrial PTSs upon the LOC indicator detection made at step 420 of FIG. 5.

Figure 6D:
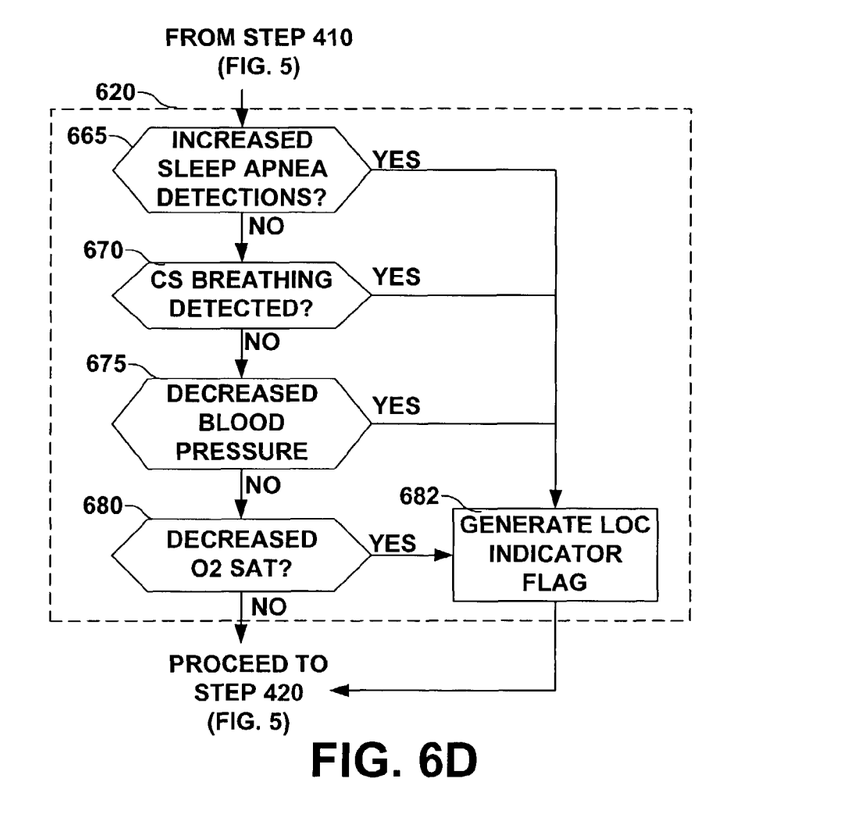

In FIG. 5, other secondary indicators of LOC based on monitoring other physiological signals may be monitored at step 620. As shown in the diagram of FIG. 6D, such physiological signals may include but are not limited to: respiration-related signals for detecting sleep apnea (step 665), Cheyne-Stokes breathing (step 670), or other cardiac-related breathing disorders; changes in blood pressure (step 675) and/or changes in blood oxygen saturation (step 680). In other embodiments, other types of physiological signals relating to hemodynamic performance, myocardial contractile function, or a metabolic state may be monitored as secondary indicators of LOC.

Atrial overdrive pacing may be provided in some patients for treating cardiac-related breathing disorders, such as sleep apnea or nocturnal Cheyne-Stokes breathing. If detection of disordered breathing episodes increases in frequency, as determined at steps 665 and/or 670, atrial overdrive pacing delivered for treating these conditions may be ineffective due to LOC. A LOC indicator flag is generated at step 682. Methods for detecting cardiac-related disordered breathing and atrial overdrive pacing for the treatment thereof are generally disclosed in U.S. patent application Ser. No. 10/419,404 to Cho et al., U.S. patent application Ser. No. 10/419,467 to Cho et al., and in U.S. Pat. No. 6,126,611 issued to Bourgeois et al., all of which are incorporated herein by reference in their entirety.

Other physiological signals, for example blood pressure and/or oxygen saturation, may be monitored for assessing the hemodynamic performance of the heart. Other types of implantable physiological sensors that may be used in conjunction with cardiac stimulation devices, besides blood pressure and oxygen saturation sensors, may include blood flow sensors, heart wall motion or acceleration sensors, acoustical sensors, or thoracic or cardiac volume (typically impedance) sensors. Examples of sensors used in implantable monitors for assessing cardiac function are described in U.S. Pat. No. 6,438,408 issued to Mulligan et al., incorporated herein by reference in its entirety. If hemodynamic performance declines during cardiac pacing according to a sensor signal, LOC may be indicated. In the embodiment shown in FIG. 6D, if blood pressure or oxygen saturation decreases, as determined at steps 675 or 680, a LOC indicator flag is generated a step 682.

Thus, other physiological signals that may be available in the implanted system may be used for monitoring secondary indicators of LOC. If any of these secondary LOC indicators are detected during cardiac pacing, for example increased episodes of cardiac-disordered breathing or decreased hemodynamic performance, a LOC warning flag may be generated at step 682, triggering a ventricular and/or atrial PTS.

Steps included in blocks 605, 610, 615, and 620 are shown in a generally sequential order in FIGS. 6A through 6D, however, all secondary indicators of LOC may be monitored in a simultaneous or near simultaneous fashion wherein the status of the secondary indicators is determined upon device interrupts. The status of secondary indicators may be determined based on a number of event counters used for tracking events related to secondary LOC indications such as: atrial refractory sensed events, PVARP extensions, events associated with patterns of retrograde conduction, number of mode switching occurrences, number of ventricular paced events during atrial pacing, number of PVCs, and/or number of cardiac-related disordered breathing episodes. The status of secondary indicators may additionally or alternatively be determined based on trends of stored data which may include lead impedance data or hemodynamic or other cardiac performance related data. Event counters or memory buffers used for temporarily storing the status of secondary indicators are reset or cleared after a secondary LOC indicator detection is made. Event counters and memory buffers may also be reset or cleared after a predetermined time interval has elapsed if counts or other stored data do not satisfy the criteria for detecting a secondary LOC indicator.

Monitoring steps shown in FIGS. 6A through 6D may be executed in an "OR" operation such that if any secondary indicator condition is satisfied, a LOC indicator flag is generated. Secondary LOC indicator conditions may be satisfied according to predetermined criteria defining a required frequency or number of incidences relating to particular events. For example, a given number of atrial refractory sensed events, PVARP extensions, mode switching occurrences, retrograde conduction events, PVCs, or ventricular paced events may be required to occur out of a given number of consecutive paced events in order to satisfy a secondary LOC indicator condition. In other examples, a minimum number of secondary LOC indicator events may be required during any given pacing episode.

In other embodiments, operations performed at decision step 420 may evaluate secondary LOC indicators in "AND" operations or combinations of "AND" and "OR" operations such that a PTS triggered by the indication of LOC based on secondary indicators depends on the detection of one or more related secondary LOC indicators. Combined detection of secondary LOC indicators may indicate a greater likelihood of either atrial or ventricular LOC and therefore trigger the first PTS in the corresponding chamber.

Thus, a system and method have been described for achieving continuous atrial and/or ventricular capture management by monitoring for secondary indicators of LOC during pacing operations. While the present invention has been described according to specific embodiments presented herein, these embodiments are intended to be exemplary, not limiting, with regard to the following claims.

What is claimed is:

1. A method of providing pacing capture management in an implantable medical device, the method comprising:
 delivering a pacing therapy through at least one lead;
 monitoring for secondary indicators of loss of pacing capture;
 performing a pacing threshold search if a secondary indicator of loss of pacing capture is monitored
 determining whether the secondary loss of pacing capture indicator more likely indicates a loss of pacing capture in an atrium or more likely indicates a loss of pacing capture in a ventricle; and
 performing the pacing threshold search on the atrium first if the secondary loss of pacing capture indicator more likely indicates a loss of pacing capture in an atrium and performing the pacing threshold search on the ventricle first if the secondary loss of pacing capture indicator more likely indicates a loss of pacing capture in a ventricle
 wherein the secondary indicators of loss of pacing capture include atrial sensed events, the atrial sensed events include an increased frequency of sensed atrial refractory events, an increased frequency of PVARP extensions, a detected pattern of retrograde conduction, an increased frequency of mode switching, or an increased duration of non-atrial tracking episodes.

2. The method of claim 1, wherein performing the pacing threshold search includes performing the threshold test on an atrium if a threshold test first performed on the ventricle fails to indicate a loss of pacing capture.

3. The method of claim 1, wherein performing the pacing threshold search includes performing the threshold test on the atrium when the threshold test first performed on the ventricle indicates loss of pacing capture if the monitoring continues to provide a secondary indicator of loss of pacing capture after a ventricular threshold has been corrected.

4. The method of claim 1, wherein pacing capture management is monitored on a continuous basis.

5. The method of claim 1, further comprising
 responding to a secondary indicator of loss of pacing capture if the pacing threshold search fails to indicate a loss of pacing capture,
 wherein responding includes one of: adjusting sensitivity levels, adjusting a refractory period, adjusting a blanking period, adjusting a pacing mode, and adjusting the delivery of pacing therapy.

6. A method of providing pacing capture management in an implantable medical device, the method comprising:
 delivering a pacing therapy through at least one lead;
 monitoring for secondary indicators of loss of pacing capture;
 performing a pacing threshold search if a secondary indicator of loss of pacing capture is monitored
 determining whether the secondary loss of pacing capture indicator more likely indicates a loss of pacing capture in an atrium or more likely indicates a loss of pacing capture in a ventricle; and
 performing the pacing threshold search on the atrium first if the secondary loss of pacing capture indicator more likely indicates a loss of pacing capture in an atrium and performing the pacing threshold search on the ventricle first if the secondary loss of pacing capture indicator more likely indicates a loss of pacing capture in a ventricle,
 wherein the secondary indicators of loss of pacing capture include one of: detecting sleep apnea, and detecting Cheyne-Stokes breathing.

7. An implantable medical device comprising:
 a pulse generator for delivering pacing pulses;
 at least one lead in electrical communication with the pulse generator for delivering the pacing pulses to cardiac tissue; and
 a microprocessor for controlling the pulse generator to generate pacing pulses according to a pacing therapy, receiving sensed data from the at least one lead, monitoring the sensed data for a secondary indicator of loss of pacing capture during the pacing therapy, determining whether the secondary loss of pacing capture indicator more likely indicates a loss of pacing capture in an atrium or more likely indicates a loss of pacing capture in a ventricle, and performing a pacing threshold search when the secondary indicator of loss of pacing capture is sensed, the pacing threshold search performed on the atrium first if the secondary loss of pacing capture indicator more likely indicates a loss of pacing capture in an atrium and the pacing threshold search performed on the ventricle first if the secondary loss of pacing capture indicator more likely indicates a loss of pacing capture in a ventricle
 wherein the secondary indicators of loss of pacing capture include one of the following: an increased frequency of sensed atrial refractory events, an increased frequency of PVARP extensions, a detected pattern of retrograde conduction, an increased frequency of mode switching, and an increased duration of non-atrial tracking episodes.

8. A method of providing pacing capture management in an implantable medical device, the method comprising:
 delivering a pacing therapy through at least one lead;
 monitoring for secondary indicators of loss of pacing capture;

performing a pacing threshold search if a secondary indicator of loss of pacing capture is monitored determining whether the secondary loss of pacing capture indicator more likely indicates a loss of pacing capture in an atrium or more likely indicates a loss of pacing capture in a ventricle; and performing the pacing threshold search on the atrium first if the secondary loss of pacing capture indicator more likely indicates a loss of pacing capture in an atrium and performing the pacing threshold search on the ventricle first if the secondary loss of pacing capture indicator more likely indicates a loss of pacing capture in a ventricle wherein the secondary indicators of loss of pacing capture include atrial sensed events, the atrial sensed events include an increased frequency of PVARP extensions.

9. A method of providing pacing capture management in an implantable medical device, the method comprising:

delivering a pacing therapy through at least one lead;

monitoring for secondary indicators of loss of pacing capture;

performing a pacing threshold search if a secondary indicator of loss of pacing capture is monitored determining whether the secondary loss of pacing capture indicator more likely indicates a loss of pacing capture in an atrium or more likely indicates a loss of pacing capture in a ventricle; and performing the pacing threshold search on the atrium first if the secondary loss of pacing capture indicator more likely indicates a loss of pacing capture in an atrium and performing the pacing threshold search on the ventricle first if the secondary loss of pacing capture indicator more likely indicates a loss of pacing capture in a ventricle wherein the secondary indicators of loss of pacing capture include atrial sensed events, the atrial sensed events include a detected pattern of retrograde conduction.

10. A method of providing pacing capture management in an implantable medical device, the method comprising:

delivering a pacing therapy through at least one lead;

monitoring for secondary indicators of loss of pacing capture;

performing a pacing threshold search if a secondary indicator of loss of pacing capture is monitored determining whether the secondary loss of pacing capture indicator more likely indicates a loss of pacing capture in an atrium or more likely indicates a loss of pacing capture in a ventricle; and performing the pacing threshold search on the atrium first if the secondary loss of pacing capture indicator more likely indicates a loss of pacing capture in an atrium and performing the pacing threshold search on the ventricle first if the secondary loss of pacing capture indicator more likely indicates a loss of pacing capture in a ventricle wherein the secondary indicators of loss of pacing capture include atrial sensed events, the atrial sensed events include an increased frequency of mode switching.

11. A method of providing pacing capture management in an implantable medical device, the method comprising:

delivering a pacing therapy through at least one lead;

monitoring for secondary indicators of loss of pacing capture;

performing a pacing threshold search if a secondary indicator of loss of pacing capture is monitored determining whether the secondary loss of pacing capture indicator more likely indicates a loss of pacing capture in an atrium or more likely indicates a loss of pacing capture in a ventricle; and performing the pacing threshold search on the atrium first if the secondary loss of pacing capture indicator more likely indicates a loss of pacing capture in an atrium and performing the pacing threshold search on the ventricle first if the secondary loss of pacing capture indicator more likely indicates a loss of pacing capture in a ventricle wherein the secondary indicators of loss of pacing capture include atrial sensed events, the atrial sensed events include an increased duration of non-atrial tracking episodes.

* * * * *